(12) United States Patent
Young et al.

(10) Patent No.: US 11,154,874 B2
(45) Date of Patent: Oct. 26, 2021

(54) FLOW MODULATION DEVICE FOR DISPENSING PRESSURIZED FLUIDS

(71) Applicant: CRYOCONCEPTS LP, Bethlehem, PA (US)

(72) Inventors: Lincoln C. Young, Bethlehem, PA (US); Philip Michael Formica, Bethlehem, PA (US); R. Sam Niedbala, Bethlehem, PA (US)

(73) Assignee: CRYOCONCEPTS LP, Bethlehem, PA (US)

( * ) Notice: Subject to any disclaimer, the term of this patent is extended or adjusted under 35 U.S.C. 154(b) by 15 days.

(21) Appl. No.: 16/717,122

(22) Filed: Dec. 17, 2019

(65) Prior Publication Data
US 2020/0188939 A1 Jun. 18, 2020

Related U.S. Application Data

(60) Provisional application No. 62/780,467, filed on Dec. 17, 2018.

(51) Int. Cl.
| | | |
|---|---|---|
| *B05B 1/02* | (2006.01) | |
| *F25B 19/00* | (2006.01) | |
| *B05B 9/04* | (2006.01) | |
| *B05B 7/24* | (2006.01) | |

(52) U.S. Cl.
CPC .................. *B05B 1/02* (2013.01); *B05B 7/24* (2013.01); *B05B 9/04* (2013.01); *F25B 19/005* (2013.01)

(58) Field of Classification Search
CPC .... B05B 1/02; B05B 9/04; B05B 7/24; B05B 15/40; F15D 1/025; F25B 19/005; A61B 17/0218
See application file for complete search history.

(56) References Cited

U.S. PATENT DOCUMENTS

| | | | |
|---|---|---|---|
| 4,865,028 A | 9/1989 | Swart | |
| 5,200,170 A | 4/1993 | McDow | |
| 5,330,745 A | 7/1994 | McDow | |
| 5,738,682 A | 4/1998 | Jensma | |
| 6,296,410 B1 | 10/2001 | Ruizendaal | |

(Continued)

OTHER PUBLICATIONS

PCT International Search Report and Written Opinion of PCT/US2019/066802 dated Feb. 28, 2020.

*Primary Examiner* — Steven M Cernoch
(74) *Attorney, Agent, or Firm* — J.A. Lindeman & Co. PLLC

(57) ABSTRACT

A flow modulation device 300 for controlling a rheological state of a dispensed pressurized fluid includes a porous element 304 and an exit tube. The porous element 304 is in fluid communication with a distal end of an outlet tube 303 and receives pressurized fluid in a first rheological state. The porous element 304 includes a plurality of channels that divide a flow channel into a plurality of flow paths through which the pressurized fluid flows and that modulates the flow of the pressurized fluid. The exit tube 305 includes proximal end 355 and distal end 345 and an intermediate body including a sidewall 365 defining a hollow internal lumen 375. The exit tube 305 is in fluid communication with the porous element 304 and receives the modulated pressurized fluid from the plurality of flow paths and refocuses the fluid to dispense the pressurized fluid in a second rheological state.

18 Claims, 7 Drawing Sheets

(56) References Cited

U.S. PATENT DOCUMENTS

| | | | |
|---|---|---|---|
| 6,960,202 B2 * | 11/2005 | Cluzeau | A61B 18/0218 |
| | | | 606/20 |
| 7,217,442 B2 * | 5/2007 | Wilt | B05B 7/2497 |
| | | | 427/385.5 |
| 7,604,632 B2 | 10/2009 | Howlett | |
| 8,038,668 B2 | 10/2011 | Scott | |
| 8,409,185 B2 * | 4/2013 | Burger | A61B 18/0218 |
| | | | 606/24 |
| 8,647,337 B2 * | 2/2014 | Niedbala | A61B 18/0218 |
| | | | 606/26 |
| 8,906,005 B2 | 12/2014 | Formica | |
| 2004/0102768 A1 | 5/2004 | Cluzeau | |
| 2007/0005048 A1 | 1/2007 | Niedbala | |
| 2010/0319360 A1 | 12/2010 | Niedbala | |
| 2014/0352794 A1 | 12/2014 | Quintard | |
| 2018/0257847 A1 | 9/2018 | Ogawa | |

* cited by examiner

FLOW MODULATION DEVICE FOR DISPENSING PRESSURIZED FLUIDS

TECHNICAL FIELD

The invention relates to devices for and methods of dispensing pressurized fluids. In particular, the invention relates to devices and methods to modulate the flow of pressurized fluids, such as liquefied gases or aerosols, from sealed containers.

BACKGROUND

Pressurized fluids such as liquefied gases and aerosols (mixtures of a pressurized gas propellant and another fluid to be dispensed) are used in industrial settings, medical treatment and in households. Pressurized fluids are typically sealed in a metal container under pressure and dispensed by opening a valve, typically a push-button or trigger valve. The pressurized fluid is dispensed from the container through a single small hole through an aperture or nozzle or through a dispenser cap connected to the valve emerging as a gaseous mist, a spray or a liquid stream. Due to the pressures within the containers and the limitations of design of the nozzle or dispenser caps, the dispensed fluids often have high flow rates (i.e., dispense rates) dictated by the pressure within the container and are difficult to control, especially when attempting to exit only a small volume or precisely direct the dispensed fluid in a desired rheological state. This can create potential safety issues or, at a minimum, makes pressurized fluids difficult to use, apply and/or control when dispensing.

SUMMARY

The invention includes a flow modulation device for controlling a rheological state of a dispensed pressurized fluid. In one example of the invention, the flow modulation device includes a porous element and an exit tube. The porous element is in fluid communication with a distal end of an outlet tube and receives pressurized fluid in a first rheological state. The porous element includes a plurality of (smaller) channels that divide a (larger) flow channel into a plurality of flow paths through which the pressurized fluid flows. The porous element modulates the flow of the pressurized fluid thereby resulting in the dispense of the materials in a desired rheological state.

In an example of the invention, the flow modulation device also includes an exit tube including proximal and distal ends and an intermediate body including a sidewall defining a hollow internal lumen. The exit tube is in fluid communication with the porous element and receives the modulated pressurized fluid from the plurality of flow paths and refocuses the fluid to dispense the pressurized fluid in a second rheological state.

In some examples of the invention, the second rheological state is a spray or droplets or a stream. For example, when the second rheological state is a spray, the spray can include droplets in a gas. In some examples, the spray is an aerosol, and in some examples, the spray is a vapor. In another example of the invention, the second rheological state is a spray including solid particles in a gas.

In some examples of the invention, the second rheological state is droplets. In other examples of the invention, the second rheological state is a stream.

In some examples of the invention, the pressurized fluid is a cryogen, a refrigerant, or a propelled material. The pressurized fluid can also be a mixture of cryogens or a mixture of refrigerants, or a mixture of propelled materials. For example, when the pressurized fluid is a cryogen or a mixture of cryogens, they can include nitrous oxide, carbon dioxide, dimethyl ether, propane, and butane.

In other examples of the invention, the pressurized fluid is a refrigerant or a mixture of refrigerants. For example, the refrigerant(s) can be tetrafluoroethane, 1,1,1-trifluoroethane, pentafluoroethane, difluoromethane, trifluoromethane, chlorodifluoromethane, and hydrofluoroolefins (e.g., 1,3,3,3-tetrafluoropropene (HFO-1234ze)). Likewise, in other examples of the invention, the pressurized fluid is a propelled material or a combination of propelled materials. Many different propelled materials can be used including food products, medicines, perfumes, cosmetics, lubricants, cleaning products, insecticides, and fuels.

The invention includes a flow modulation device for controlling a rheological state of a dispensed pressurized fluid. In some examples of the invention, the flow modulation device includes a porous element and an exit tube. The porous element is in fluid communication with a distal end of an outlet tube. The porous element receives pressurized fluid in a first rheological state. The porous element includes a plurality of channels that divide a flow channel into a plurality of flow paths through which the pressurized fluid flows and that modulate the flow of the pressurized fluid. The exit tube includes proximal and distal ends and an intermediate body that includes a sidewall defining a hollow internal lumen. The exit tube is in fluid communication with the porous element and receives the modulated pressurized fluid from the plurality of flow paths and refocuses the fluid to dispense the pressurized fluid in a second rheological state. In example embodiments of the invention, the first rheological state is a pressurized fluid, and the second rheological state is one of a spray, or of droplets, or of a stream. In example embodiments of the invention, the second rheological state is a spray including droplets in a gas or a spray that includes an aerosol, or a spray that includes a vapor.

In some example embodiments of the invention, the second rheological state is a spray that includes solid particles in a gas, and in other examples of the invention, the second rheological state is droplets. The second rheological state is a stream in some examples of the invention.

In examples of the invention, the pressurized fluid is a cryogen, a refrigerant, or a propelled material which is miscible, not miscible, or expressed from a bag. In other examples of the invention, the pressurized fluid is a cryogen or a mixture of cryogens that includes at least one selected from the group of nitrous oxide, carbon dioxide, dimethyl ether, propane, and butane.

In example embodiments of the invention, the pressurized fluid is a refrigerant or a combination of refrigerants that includes at least one selected from the group of a chlorofluorocarbon (CFC), a hydrochlorofluorocarbon (HCFC), and hydrofluoroolefins, while in other examples of the invention, the pressurized fluid is at least one selected from the group of tetrafluoroethane, 1,1,1,-trifluoroethane, pentafluoroethane, difluoromethane, trifluoromethane, chlorodifluoromethane and hydrofluoroolefins.

The invention includes examples where the pressurized fluid is a propelled material that includes at least one selected from the group of a food product, a medicine, a perfume, a cosmetic, a lubricant, a cleaning product, an insecticide, and a fuel.

In example embodiments of the invention, the porous element includes at least one selected from the group of a porous plastic, a porous glass, a sintered metal, and a packaged porous particle in the shape of the flow channel.

The invention also includes methods of modulating the flow for controlling a rheological state of a dispensed pressurized fluid. Methods in accordance with the invention include flowing the pressurized fluid through an outlet tube to create a flow channel, receiving the pressurized fluid in a first rheological state from the flow channel with a porous element, and dividing (with the porous element) the flow channel into a plurality of flow paths through which the pressurized fluid flows through the porous element. The methods also include modulating the flow of the pressurized fluid with the plurality of flow paths, receiving the modulated pressurized fluid from the plurality of flow paths with an exit tube, and refocusing (with the exit tube) the modulated pressurized fluid from the plurality of flow paths. The methods also include dispensing the pressurized fluid in a second rheological state.

In some embodiments of the invention, the second rheological state is a spray or droplets or a stream, and in other embodiments of the invention, the second rheological state is a spray including droplets in a gas or a spray including solid particles in a gas. In some examples of the invention, the spray is an aerosol, and in other examples, the spray is a vapor.

In examples of the invention, the methods utilize pressurized fluid that is a cryogen, a refrigerant, or a propelled material which is miscible, not miscible, or expressed from a bag. In other examples of the invention, the methods utilize pressurized fluid is a cryogen or a mixture of cryogens that includes at least one selected from the group of nitrous oxide, carbon dioxide, dimethyl ether, propane, and butane.

In example embodiments of the invention, the methods utilize a pressurized fluid that is a refrigerant or a combination of refrigerants that includes at least one selected from the group of a chlorofluorocarbon (CFC), a hydrochlorofluorocarbon (HCFC), and hydrofluoroolefins, while in other examples of the invention, the pressurized fluid is at least one selected from the group of tetrafluoroethane, 1,1,1,-trifluoroethane, pentafluoroethane, difluoromethane, trifluoromethane, chlorodifluoromethane and hydrofluoroolefins.

The invention includes example methods where the pressurized fluid is a propelled material that includes at least one selected from the group of a food product, a medicine, a perfume, a cosmetic, a lubricant, a cleaning product, an insecticide, and a fuel.

In example embodiments of the invention, the methods include use of a porous element that includes at least one selected from the group of a porous plastic, a porous glass, a sintered metal, and a packaged porous particle in the shape of the flow channel.

Example embodiments of the invention include methods for controlling a rheological state of a dispensed pressurized fluid. The methods include (a) selecting a pressurized fluid including a known fluid at a known pressure; (b) selecting a desired rheological state which the selected pressurized fluid exhibits when dispensed; (c) receiving the selected pressurized fluid in a first rheological state and an initial flow rate with a porous element having a known pore size, a known diameter, and a known length; (d) modulating the received pressurized fluid with the porous element to reduce the pressure of the pressurized fluid exiting the porous element and to reduce the initial flow rate of the pressurized fluid; (e) receiving the pressurized fluid at the reduced flow rate at a proximal end of an exit tube having a known inside diameter and a known length; (f) transitioning the first rheological state of the received pressurized fluid into a second rheological state of the received pressurized fluid at a distal end of the exit tube; and (g) dispensing the received flowed pressurized fluid at a distal end of the exit tube in a desired second rheological state and reduced flow rate.

In example embodiments of the invention, the methods for controlling a rheological state of a dispensed pressurized fluid further include (h) selecting an alternative porous element with at least one selected from the group of an alternative pore size different from the known pore size, an alternative diameter different from the known diameter (width), and an alternative length different from the known length; (i) receiving the selected pressurized fluid in the first rheological state and the initial flow rate with the alternative porous element when modulating the received pressurized fluid in step (d) results in an undesirable reduced flow rate or an undesirable second rheological state; and (j) repeating steps (d)-(g) using the alternative porous element.

In example embodiments of the invention, the methods for controlling a rheological state of a dispensed pressurized fluid of claim 101 also include (k) selecting an alternative exit tube wherein the alternative exit tube includes at least one selected from the group of an alternative inside diameter and an alternative length, and receiving the pressurized fluid at a proximal end of the alternative exit tube when dispensing the received pressurized fluid in step (g) results in a second rheological state different than the desired second rheological state; and (l) repeating steps (e)-(g) using the alternative exit tube.

The invention provides a safe, effective, and efficient manner for controlling a rheological state of a dispensed pressurized fluid using flow modulation devices that include a porous element and an exit tube. The invention provides devices and methods for dispensing pressurized fluids such as liquefied gases and aerosols (mixtures of a pressurized gas propellant and another fluid to be dispensed) used in industrial settings, medical treatments, and in households. The invention overcomes the high pressures of pressurized fluid containers and the limitations of designs of the nozzles and/or dispenser caps. The invention provides devices and methods for controlling the rheological states of the dispensed fluids and makes it possible to dispense only a small volume or precisely direct the dispensed fluid in a desired rheological state.

DETAILED DESCRIPTION

Figure 1:
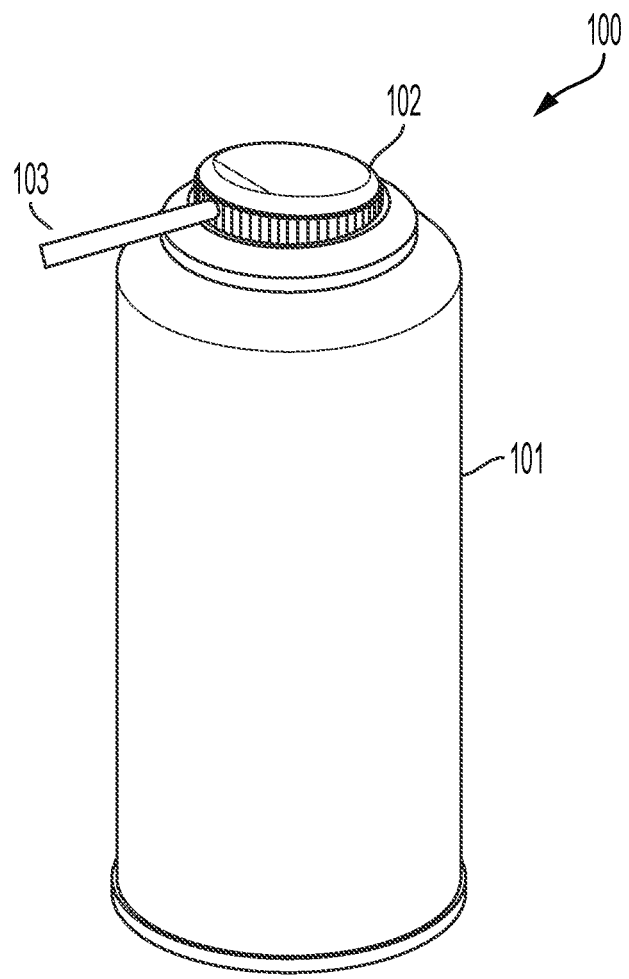
FIG. 1 shows a view of a sealed container system in accordance with the invention for dispensing a pressurized fluid.

The invention relates to devices and methods to modulate the flow of pressurized fluids, such as liquefied gases, and aerosols or other pressurized fluids, from sealed containers. In known devices the control of flow of a pressurized fluid is usually based upon the inner diameter of the passageway the fluid will follow. The speed of flow is controlled by this single lumen and highly influenced by the internal pressure of the fluid within the canister. These prior systems were also susceptible to clogging due to impurities or particulates in the pressurized fluid. This invention instead uses a combination of a porous element and an exit tube to modulate the flow of a pressurized fluid and to control the manner in which the fluid is dispensed. The porous element includes a multitude of channels followed by an exit tube lumen that, in combination, allows desired control of the pressurized fluid being dispensed. The pore size, percent porosity, and thickness (length) of the porous element, along with the internal diameter and length of the exit tube are adjusted to achieve a desired rheological state for the pressurized fluid output.

This invention modulates the flow of pressurized fluids to affect a rheological change in the fluids as they are dispensed. The invention controls the flow rate (dispense rate) and flow volume and pressure to dispense the pressurized fluid in a desired rheological state, including a vapor (gas), spray, and liquid. By means of the invention a pressurized fluid may exit an apparatus in a controlled and in as-desired manner, that is, as a vapor or as a higher flow stream of particles or as larger droplets mixed with a stream of small droplets or until finally the pressurized fluids flows and behaves as a liquid. Thus, the control of the state of pressurized fluids can be achieved in a variety of uses where the dispensed fluid flow requires variation from a spray to droplets. And, the devices and methods of the invention accomplish this flow control at low cost.

A flow modulation device and method of the invention creates a change in pressure, speed, and volume in the flow channel of pressurized fluids that enables (in some cases) a phase change and subsequent exit of pressurized fluid (i.e., the material delivered from the container) to control its exit from the dispensing container. The invention includes a porous element that divides the flow channel into a multitude (e.g. hundreds or thousands) of flow paths made up of small and sometimes varying length channels within the porous element thus modulating the flow velocity and volume and pressure of the (flowing) pressurized fluid. As the flow velocity and volume of the pressurized fluid flowing into the channels changes, the surface tension of the pressurized fluid changes leading to a change in the rheological state of the fluid. Beyond the porous element, the fluid encounters an exit tube which acts as a secondary channel refocusing the fluid within its lumen. The lumen diameter and length then dictates the final fluid velocity and pressure, controlling the rheological state of the dispensed fluid—from droplets (lower velocity) to a stream to a spray (higher velocity). Thus, dispensing a pressurized fluid through the combination of the porous element and the lumen of the exit tube provides control over the rheological state of the dispensed fluid depending on the pore size, percent porosity, and thickness (length) of the porous element, along with internal diameter and length of the exit tube selected to achieve a desired pressurized fluid output.

In current systems, the control of flow of a pressurized fluid is usually based upon the inner diameter of the passageway the pressurized fluid will follow as it exits a container. The flow is then facilitated by this single lumen until the pressurized fluid exits the assembly. In contrast, the devices and methods of this invention use a combination of a porous element and an output tube to affect a change in the rheological state of the pressurized fluid. A multitude of channels (including channels of varying length) within the porous element followed by lumen dimensions of an exit tube allows the control of pressurized gas fluid. In this way the pressurized fluid may exit the container in a variety of controlled rheological states, e.g., as a spray, as a higher flow stream of droplets, as larger droplets mixed with a stream of small droplets, or where the pressurized fluid flows and behaves as a liquid. Thus, the devices and methods of the invention control the rheological state of the dispensed pressurized fluid.

FIG. 1 shows a view of a typical sealed container system 100 for dispensing a pressurized fluid. The system 100 includes a canister 101 which contains the pressurized fluid to be dispensed by the system, such as a refrigerant or cryogen or propellant or other material. Generally, the canister 101 contains a pressurized fluid as a liquefied gas or an aerosol which may be a mixture of a gas propellant and another fluid to be dispensed or a pressurized container with a bag from which product is expelled through the flow control path. For an aerosol the gas propellant may be a standard, pressurized gas propellant, or air that is pumped into the canister by the user. For the purposes of a non-limiting example, it can be assumed that the canister 101 in FIG. 1 contains a pressurized fluid and is not pumped to create pressure inside the canister. A valve actuator 102 (for example, as a push button) is coupled to a valve stem and valve mechanism (not shown separately). The valve actuator 102 extends up from a top of the canister 101 in a conventional manner. The valve actuator 102, which may be any actuator known in the art, includes a body having a channel that receives, and couples to the valve stem, and forms a passageway to an outlet, shown here as an outlet tube 103. The outlet can also be an aperture or nozzle into which a tube, such as outlet tube 103, may be inserted. Manipulating the valve actuator 102 allows a user to open/close a valve of the canister 102 and to cause the pressurized fluid therein to escape out the valve stem and through the outlet tube 103, depicted here, or an aperture/nozzle (not shown separately).

Figure 2:
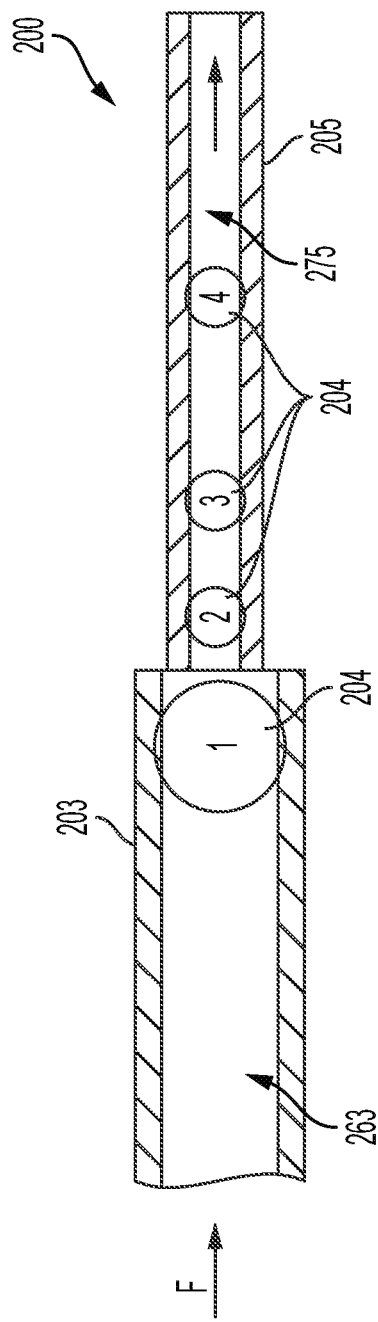
FIG. 2 depicts a cross-sectional view of a flow modulation device in accordance with the invention for a container system dispensing a pressurized fluid such as shown in FIG. 1.

FIG. 2 depicts a cross-sectional view of a flow modulation device for a container system dispensing a pressurized fluid such as shown in FIG. 1. A flow modulation device 200 of the invention comprises a porous element 204 and an exit tube 205 in flow communication with the porous element 204. The flow modulation device 200 may be attached to an outlet tube 203 such that the porous element is disposed in the flow channel of the fluid when dispensed from a container (not shown) through an outlet tube 203, and an exit tube 205 opposite the outlet tube 203 and in the same flow channel with the porous element 204. As shown, when dispensed the pressurized fluid flows, as shown with directional arrow F, from the outlet tube 203 through the porous element 204 and out the exit tube 205. A flow modulation device according to the invention, as depicted in any of the FIGS., need not be straight or rigid and may be curved or flexible to conform to a desired shape as long as the flow paths described are maintained. FIG. 2 shows four possible positions for the porous element 204. The porous element 204 may be placed anywhere in the flow channel, for example, at a location within the outlet tube 203, position 1; at a location in between the outlet tube 203 and the exit tube 205, position 2; at a location inside the exit tube 205 at the end adjacent to the outlet of the outlet tube 203, position 3; or at a location within the exit tube 205 downstream of the outlet of the outlet tube 203, position 4.

Figure 3:
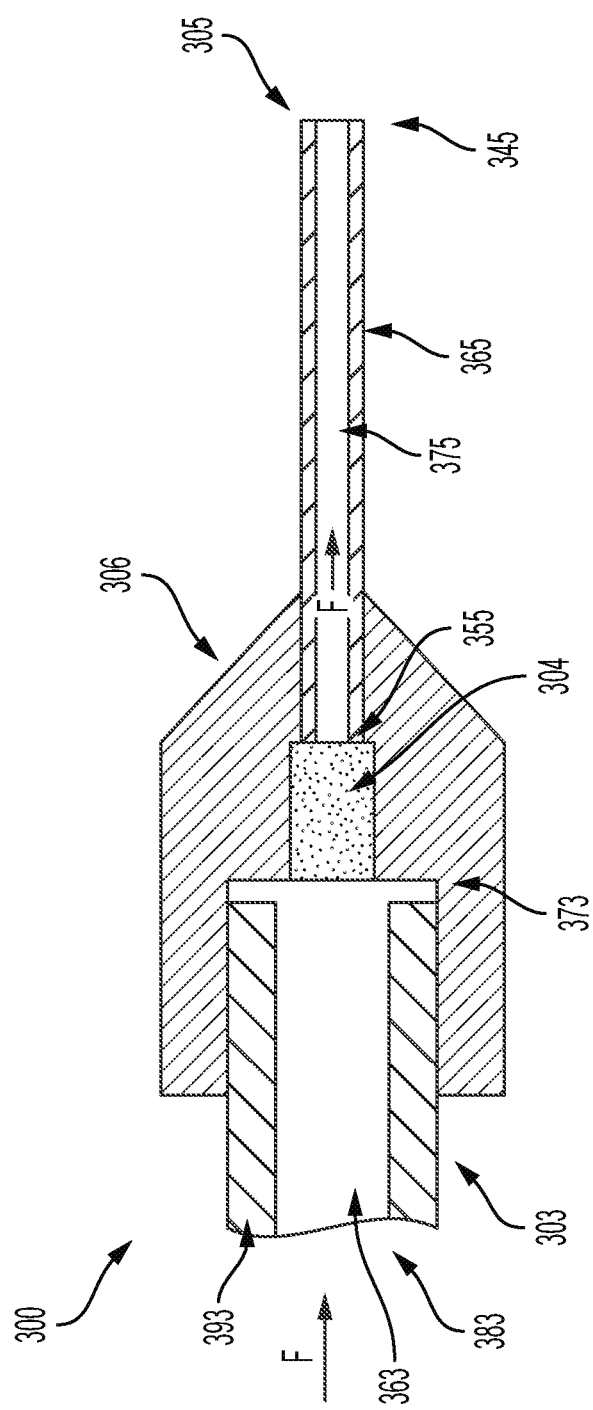
FIG. 3 illustrates a cross-sectional view of an exemplary flow modulation device of the invention with a porous element between the outlet tube and the exit tube.

FIG. 3 depicts a cross-sectional view of an exemplary flow modulation device 300 of the invention with the porous element 304 in position 2 as shown in FIG. 2 (between the outlet tube 303 and the exit tube 305). The porous element 304 and the proximal end 355 of the exit tube 305 are contained within a housing 306, which attaches to the distal end 373 of the outlet tube 303. In FIG. 3, the housing 306 is fitted over the terminal portion (distal end 373) of the outlet tube 303 and the flow modulation device 300 held in place by friction, by other mechanical means, or by using an adhesive. For example, the housing 306 may be screwed onto to the outlet tube 303, clamped, or secured by other mechanical means known in the art. The materials used for the outlet tube 303 and the housing 306, as well as the means by which they are fit together, are capable of handing the pressure created behind the porous element 304. As shown by the directional F arrow in FIG. 3, pressurized fluid flows from a container (not shown) between the sidewalls 393 of the proximal end 383 of the outlet tube 303 to the distal end 373 of the outlet tube 303. From there, the pressurized fluid flows through the porous element 304 and between the sidewalls 365 of the proximal end 355 of the exit tube 305 through the hollow internal lumen 375 to the distal end 345 of the exit tube 305.

Figure 4:
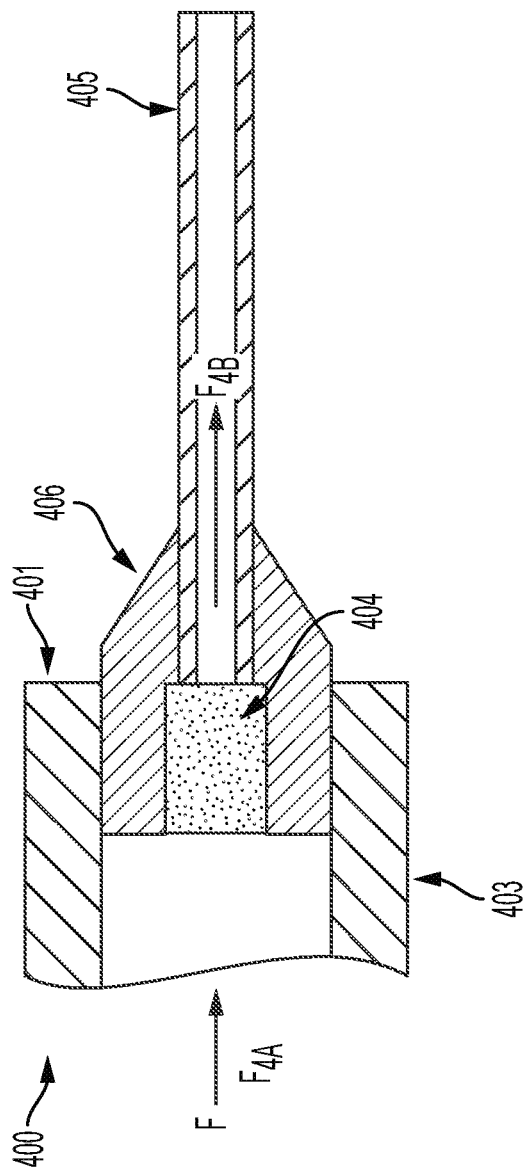
FIG. 4 shows a cross-sectional view of a container system in accordance with the invention with the outlet of the container system as an aperture/nozzle) and the housing sized to fit within the aperture.

As shown in the cross-sectional view of FIG. 4, when the outlet of a container system is an aperture (or a nozzle) 401, and not an outlet tube 303 as depicted in FIG. 3, the housing 406 is sized to fit within the aperture 401, and the flow modulation device 400 can be held in place as described above. When dispensed, the pressurized fluid flows F in the direction $F_{4A}$ shown in FIG. 4. Any dead space between the outlet tube 403 or the aperture of 401 and the porous element 404 should be minimized to allow the pressurized fluid to flow easily through an outlet, such as outlet tube 403, through the porous element 404 and as $F_{4B}$ out the exit tube 405.

As discussed above, the invention modulates the pressure, speed, and volume of a high-pressure fluid such that the fluid is dispensed in a controlled manner. The devices and methods of the invention place a porous element in the fluid flow channel. The porous element divides the flow channel into a multitude (e.g., tens or hundreds or thousands) of flow paths made up of small and sometimes varying length channels within the porous element. As the flow velocity and pressure of the pressurized fluid flowing into the channels changes, the rheological state of the pressurized fluid changes. As the flow velocity and pressure of the high-pressure fluid changes, the volumetric flow is adjusted to dispense the high-pressure fluid in various rheological states. The invention creates a dispensed fluid with a desired rheological state ranging from a spray to droplets at the outlet.

A number of different porous element materials may be used in a device or method of the invention. Suitable materials include, but are not limited to, porous plastics, porous polymers, porous glass, sintered metals, packed porous particles, packed particulates such as sand, or other materials capable of forming porous channels. While the porous element often can be a cylindrical shape when used with devices having round tubes, the porous element may be any three-dimensional shape suitable for its placement in the flow channel of the pressurized fluid. For example, when placed in position 1 of FIG. 2, the porous element 204 has a cross-sectional area (perpendicular to the flow channel) that is approximately the same size as the diameter of hollow internal channel 263 of the outlet tube 203 and larger than the diameter of hollow internal lumen 275 of the exit tube 205. When placed in position 2 of FIG. 2, the porous element 204 can have a cross-sectional area that is less than or equal to the diameter of the hollow internal channel 263 of the outlet tube 203 and greater than or equal to the diameter of the hollow internal lumen 275 of the exit tube 205. When placed in positions 3 or 4 of FIG. 2, the porous element 204 has a cross-sectional area approximately the same size or smaller as the diameter of hollow internal lumen 275 of the exit tube 205. With other holders, the porous element can be sized accordingly to create a plurality of flow paths through the flow channel of the device 200. The porous elements used in accordance with the invention include pore sizes of 0.5 microns and larger, diameters (widths) of 250 microns and larger, and thicknesses (lengths) of 100 microns and larger. The scale of the system will inform the selection of porous elements, including pore size, diameter, and thickness (e.g., larger systems use larger porous elements, even on the scale of centimeters and larger). In the examples of the invention using the pressurized fluids as described below, the porous elements included pore sizes from 2 microns to 20 microns. The porous elements used in the examples of the invention using the pressurized fluids as described below included diameters (widths) (i.e., "diameters" when the porous elements are round and "width" when they are not round) of 1.5 mm to 3 mm and thicknesses (lengths) of 1.5 mm to 3 mm. Other pressurized fluids utilize similar parameters but may differ in orders of magnitude.

As the pressurized fluid flows beyond the porous element, the pressurized fluid flows into an exit tube such as described above. The exit tube may be made from materials such as plastics or metals capable of withstanding the pressures and temperatures of the pressurized fluids. The exit tube is sized (internal diameter and length) to facilitate conversion of the pressurized fluid from a first rheological state, such as a liquid or liquid-gas mixture to a second rheological state, such as a spray, droplets, or stream based on the physical characteristics of the porous element described above (e.g., pore size, percent porosity, and thickness). The exit tube, in combination with the porous element, achieves the desired second rheological state. The exit tubes used in accordance with the invention include inside diameters of 50 microns and larger and lengths of 10 millimeters and larger. In the examples of the invention using the pressurized fluids as described below, the exit tubes included inside diameters from 250 microns to 2 millimeters and lengths of 10 millimeters to 400 millimeters. Other pressurized fluids utilize similar parameters but may differ in orders of magnitude.

The exit tube may also control the heat flux (e.g., insulate) in the flow paths keeping the pressurized fluid in the desired second rheological state. Thus, the exit tube acts as a secondary channel element refocusing the fluids into the lumen of the exit tube and dictating the final fluid velocity. The dispensed fluid leaves the exit tube in a controlled manner ranging from droplets (low velocity) to a stream (higher velocity). Thus, the combination of the porous element and the exit tube provides control over the dispensing of pressurized fluids.

The modulated flow devices and methods of the invention may be used to control the phase of a pressurized fluid from a sealed canister. The pressurized fluid may be a refrigerant, an aerosol such as an oil as in the WD-40® product, or a cryogen gas dispensed in a cryosurgical procedure.

The use of a flow modulation device and method in cryosurgical devices and for cryosurgery are preferred exemplary embodiments of the invention. A flow modulation system of the invention may be used with any cryosurgical device which dispenses a cryogen as a pressurized fluid. The flow modulation device and methods are particularly useful in applicator-based cryosurgical devices and with a cone-based cryosurgical device and overcomes deficiencies and limitation of use in each.

Applicator-based cryosurgical devices have an absorbent applicator at the end of an outlet tube. Applicator-based cryosurgical devices are known in the art and described, for example, in U.S. Pat. Nos. 4,865,028; 5,738,682; 6,296,410; 7,604,632; 8,038,668; and 8,906,005—the disclosures of which are incorporated herein by reference. In an applicator-based system, the treatment applicator (typically cotton and/or open cell foam) is typically attached to the end of a tube, which is inserted directly into the outlet port of a high-pressure canister. When used, the absorbent applicator receives and fills with the cryogen after which the filled applicator is pressed against the lesion or area being treated. However, the full pressure of the spray-can pushes cryogen into and through the applicator material which has a defined holding capacity based on the size and type of applicator material. High-pressure pushing of the cryogen though the applicator or leaking from the applicator limits the efficiency and efficacy of an applicator-based system and often creates a significant waste of the cryogen. The applicator's ability to reach and hold the lowest temperature for a sufficiently long period of time (efficacy impact) is dependent on the amount of cryogen "captured" and held within the applicator material. Cryogen sprayed into the air or leaked evaporates and is lost.

A cryosurgical device with a flow modulator of the invention can have an absorbent applicator at the distal end of the exit tube. Modulating the flow of the cryogen from the container to the applicator permits better and more efficient filling of the absorbent applicator and avoids blow-by, leakage and waste. For example, lower boiling point cryogens typically result in high pressure in the containers, which makes controlled dispensing of the cryogens even more difficult. Modulating the flow improves the overall efficiency and efficacy of the applicator-based cryosurgical device. Accordingly, the invention relates to an improved applicator-based cryosurgical device where the outlet of the container, from which the cryogen leaves when released, is in fluid communication with a porous element followed by an exit tube and where the terminal end (distal end 345) of the exit tube is in fluid communication with an absorbent applicator. In a cryosurgical device of the invention, the cryogen flows from its container through a porous element, then into the exit tube and fills the absorbent applicator at the end of the exit tube. In a device or method of the invention, the cryogen fills the absorbent applicator at a slower more controlled flow rate (dispense rate) of liquid cryogen. The filled absorbent applicator is then used to treat a lesion, or an area of the skin as is known in the art.

Other cryosurgical devices place a receptacle around the lesion or area to be treated then spray cryogen into the receptacle. In this invention, the receptacle can be attached to the exit tube or hand-held as a separate device. Examples of receptacles that are attached to the exit tube are described in U.S. Patent Application Publication No. US 2007/0005048. Examples of separate hand-held devices are known in the art and described, for example, in U.S. Pat. Nos. 5,200,170 and 5,330,745—the disclosures of which are incorporated herein by reference in their entirety. When held in one hand, high pressure in the canister makes it difficult to control the cryogen as it is sprayed into a cone being held against a patient's skin with the other hand. There is a significant risk of spraying and splashing of the cryogen out of the top of the cone during dispense (which may land on and freeze-burn the doctor and/or the patient). Controlling the cryogen to avoid spraying and splashing is especially critical when treating pediatric patients. With cone systems, doctors must look down into the cone to estimate the amount of cryogen dispensed, and during longer dispense times, the high flow rate (dispense rate) causes the cryogen container to get extremely cold and difficult to hold.

Fluid modulation of the cryogen according to the invention allows for more controlled delivery of the cryogen into the cone and onto the lesion or area being treated. Modulating the flow of the cryogen from the container to the applicator permits better and more efficient filling of the cone surrounding the area to be treated and avoids spraying, splashing, and leakage. This improves the overall efficiency and efficacy of the cone-based cryosurgical system as well as patient and doctor safety. Accordingly, the invention relates to an improved cone-based cryosurgical system where the outlet of the container, from which the cryogen leaves when released, is in flow communication with a porous element followed by an exit tube. In a cryosurgical device of the invention, the cryogen flows from its container through a porous element, then through the exit tube and then is directed to fill a cone or receptacle placed on an area for treatment. The filled cone or receptacle is then used to treat a lesion or an area of the skin as is known in the art. The cone or receptacle is capable of holding the pressurized fluid that is delivered and allowing it to evaporate or act in a controlled manner delivering a desired amount to the target area where applied.

Figure 5:
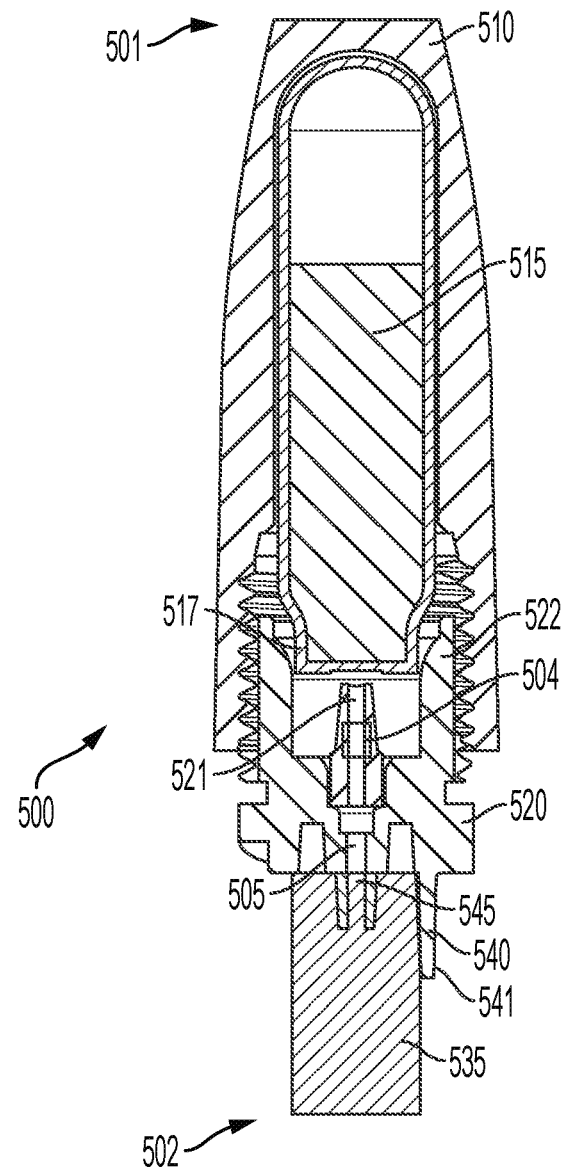
FIG. 5 shows an example of single-use device in accordance with the invention assembled and ready for operation.
Figure 6:
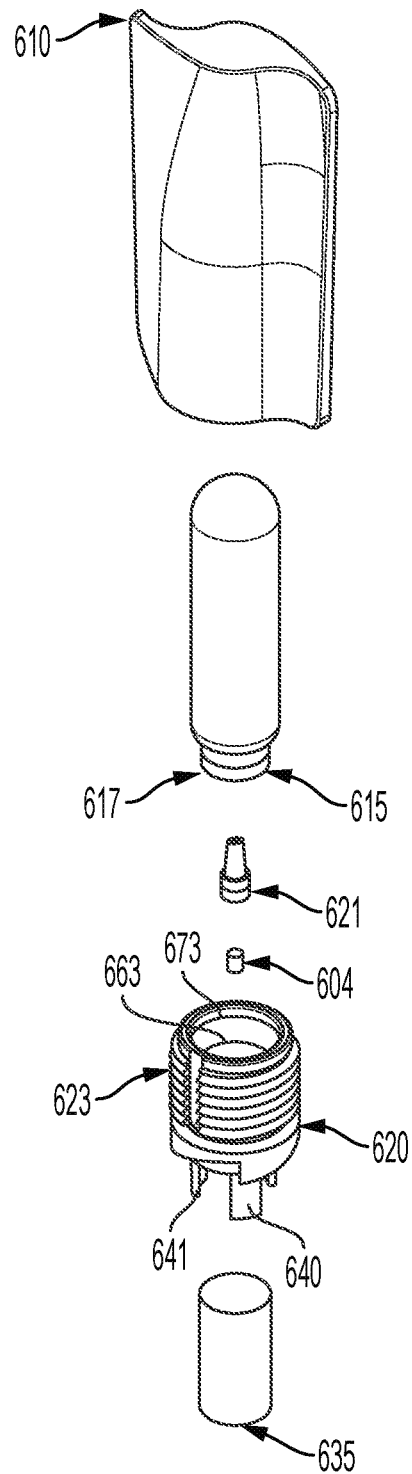
FIG. 6 shows an exploded view of a device in accordance with the invention with the device components.

While the invention has been described with regard to dispensing pressurized fluids from containers having valves, the flow modulation devices and methods of the invention may also be used in so-called, single use devices. In a single-use device the pressurized fluid is contained within a sealed container. Breaking the seal, typically by a hollow piercing member such as a pointed tube, releases the pressurized fluid to flow along a flow channel through, for example, the hollow piercing member. FIGS. 5 and 6 show an example single use device 500, 600 in accordance with the invention, the hollow piercing member 521, 621 or other tube in flow communication with the sealed container (single use cryogen cylinder 515, 615). In a single use device 500, 600, the seal of the single use cylinder 515, 615 may be broken, as is known in the art, by punching, screwing or otherwise forcing a piercing member 521, 621 through the seal of the single use cylinder 515, 615.

FIG. 5 shows an example of single-use device 500 of the invention assembled and ready for operation. The exemplary single-use device 500 depicted is an applicator-based cryosurgical device. FIG. 6 shows an exploded view of the device 600 with the device components. As shown in FIGS. 5 and 6, the invention includes an upper housing 510, 610, a lower housing 520, 620, a single use cylinder 515, 615 filled with a pressurized fluid such as a cryogen, a porous element 504, 604, an exit tube 505, and an applicator 535, 635. Upper housing 510, 610 receives single use cylinder 515, 615 filled with cryogen.

A single use cylinder 515, 615 filled with cryogen is inserted into upper housing 510, 610 with the neck 517, 617 of the cylinder 515, 615 protruding from upper housing 510, 610 away from the top 501. In an example of the invention shown in FIG. 6, the lower housing 620 can be joined to the upper housing 610 using a screw-type connection 623. In either case, lower housing 520, 620 includes a central piercing member 521, 621 that is aligned coaxially with the neck 517, 617 of cylinder 515, 615. Central piercing member 521, 621 ultimately pierces the sealed neck 517, 617 of the single use cylinder 515, 615 to release the cryogen.

A porous element 504, 604 is in the flow channel of the device 500, 600 and can be located in either the piercing projection 521, 621 or in the exit tube 505. The porous element 504, 604, in combination with exit tube 505, modulates the pressure, speed, and volume of the high-pressure fluid in the flow channel to control the rheological state of the dispensed material. In any case, the porous element 504, 604 is placed in the flow channel of the pressurized fluid as the cryogen flows from the cylinder 515, 615 to the distal end 545 of the exit tube 505.

The lower housing 520, 620 also includes an applicator housing 540, 640 that includes a central opening (not shown separately) and extends from the lower housing 520, 620. Applicator housing 540, 640 includes housing projections 541, 641 that form a concentric circle about the central opening of the applicator housing 540, 640. Applicator housing 540, 640 is positioned over the distal end 545 of exit tube 505, and housing projections 541, 641 of the applicator housing 540, 640 receive applicator 535, 635 and hold it securely using pressure from housing projections 541, 641 acting upon the applicator 535, 635.

Once the components are assembled as described above, an optional base (not shown in the FIGS.) can be placed over the combination of the applicator 535, 635, exit tube 505, porous element 504, 604, and lower housing 520, 620. The device 500 is fully assembled as shown in FIG. 5.

The optional base (not shown) can hold and protect the applicator 535, 635 during activation of the device 500, 600. In operation, when a base covering the device 500 (i.e., bottom 502 of the device 500) is resting on a hard surface, a user screws the lower housing 520 into upper housing 510 of the device 500. As the upper housing 510 screws into the lower housing 520, the piercing member 521 contacts the single use cylinder 515 at the neck 517 of the cylinder 515. As the screw connection is made, the piercing member 521 is driven further and pierces a single use cryogen cylinder 515. The upper housing 510 and lower housing 520 are now screwed together and latched via reciprocal connection projections (as described above) that mate.

Similarly, as shown in FIG. 6, the cryogen cylinder 615 can be pierced using a mutually engageable screw threading that enables lower housing 620 to be moved (e.g., loosened from and tightened onto) the upper housing 610. In one exemplary embodiment of the invention shown in FIG. 6, screw type connection 623 may be provided on an external surface of the lower housing 620 and configured to engage with screw threading (not shown separately) on an inner surface of the upper housing 610. To first use the device 600, an operator may tighten lower housing 620 into the upper housing 610 by turning the screw-type connection 623. The lower housing 620 may define a recess 663 configured to receive at least a portion of a neck 617 of the single-use cylinder 615 when the combination of the upper housing 610 and the lower housing 620 is tightened (screwed) into the upper housing 610. The lower housing 620 may further include a hollow piercing projection 621 at least partially disposed in the recess 663 and configured to puncture a seal of the single-use cylinder 615, placing the cryogen reservoir of the single-use cylinder 615 in flow communication with the porous element, exit tube (not shown in FIG. 6) and applicator 635. Disposed in the recess 663 surrounding the hollow piercing projection 621 is a sealing member 673, which may be a compression seal for example, configured to substantially prevent the cryogenic fluid from leaking as it flows from the reservoir of the single-use cylinder 615 through the hollow piercing projection 621.

In any case, as the upper housing 510 and lower housing 520 mate and latch, and the piercing member 521, 621 pierces the single use cryogen cylinder 515, 615, the cryogen flows through porous element 504, 604 into the exit tube 505, 605 of the device 500, 600. As outlined above, a latching mechanism ensures that the consumer cannot access the high-pressure cylinder 515, 615 after it is pierced but is still pressurized.

The cryogen flows through the porous element 504, 604 and the exit tube 505, 605 to the applicator 535, 635, which can be positioned over an affected area to be treated. Once the cryogen saturates the applicator 535, 635, the applicator 535, 635 is placed in contact with the affected area to cause freezing of the affected area. The low temperature of the cryogen ensures that the applicator 535, 635 is immediately ready for use. Once saturated, the applicator 535, 635 remains at effective temperatures for several minutes.

Once the treatment is complete, the single-use device is now spent and may be disposed of in the regular trash. The use of the applicator 535, 635 minimizes the risk of spraying of cryogen on healthy skin. In addition, the material of the applicator 535, 635 can be trimmed, or re-sized with scissors to match the size of a skin lesion. This minimizes the treatment of healthy skin while treating the target lesion.

EXAMPLE 1

Nitrous Oxide (N2O) and Carbon Dioxide (CO2)

The following experiments were performed with each gas/product to demonstrate the ability to control the type of fluid dispensed. The pressure drop in the porous material was performed using porous plastics of various porosities, diameters (widths), thicknesses (lengths), and stacked combinations with exit tubing having a variety of inner diameters.

A porous polymeric material was used as the porous element (ME). The porous polymeric material is supplied with specifications for Pore Size, Porosity, Thickness and Air Flow. The porous polymeric material is made into a matrix containing thousands of porous channels. Changing the combination of porous materials and exit tube (ID and length), the high-pressure fluids may be made to exit at any desired rate. Table 1 below provides example specifications of porous material (PM) used.

TABLE 1

Examples of Porous Material (PM) Used

| PE (porous element) | Pore Size (microns) | Porosity % | Thickness (in) | Thickness (mm) |
| --- | --- | --- | --- | --- |
| PM-1 | 3-5 | 30-40 | 0.059 | 1.5 |
| PM-2 | 4-7 | 40-45 | 0.059 | 1.5 |
| PM-3 | 7-14 | 45-55 | 0.059 | 1.5 |
| PM-4 | 12-25 | 50-60 | 0.059 | 1.5 |
| PM-5 | 25-35 | 55-60 | 0.059 | 1.5 |
| PM-6 | 30-60 | 50-60 | 0.059 | 1.5 |
| PM-7 | 1-3 | 25-30 | 0.079 | 2 |
| PM-8 | 3-5 | 30-40 | 0.04 | 1 |

A model flow modulation in accordance with the invention was created to spray two pressurized fluids used in cryosurgical devices, N₂O gas or CO₂ gas. A cryosurgical device dispenses a gaseous stream of cryosurgical fluid to deliver it to the surface of skin in order to freeze targeted tissues and lesions. This example demonstrates how the flow modulation system of the invention operates with various porous elements (e.g., porous plastics) having different porosities and various exit tube inner diameters to control the characteristics of the dispensed fluids.

Figure 7:
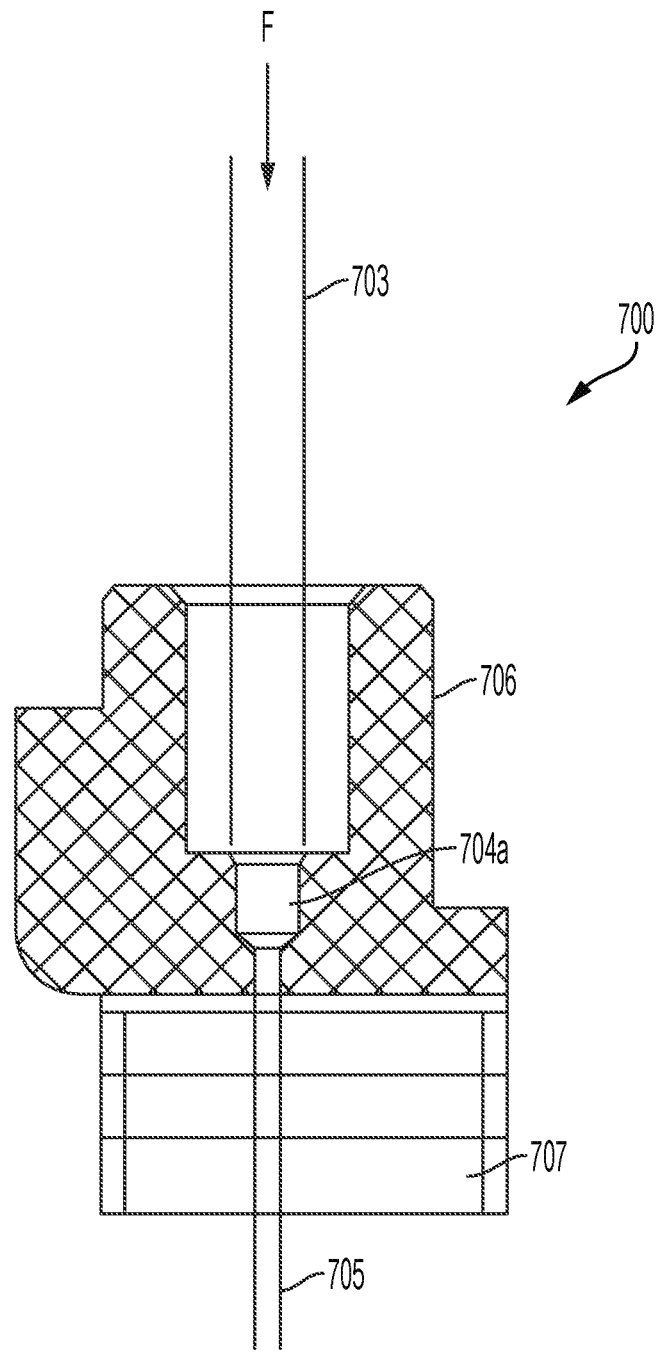
FIG. 7 shows porous elements that were cut using a punch and installed in an assembled flow modulation device in accordance with the invention.

Briefly, and as shown in FIG. 7, the porous elements were cut using a punch and installed in an assembled flow modulation device 700, with the valve slide 706 placed over an outlet tube 703 as shown in FIG. 7. The valve slide 706 had an outlet tube 703 used to pierce a sealed container, a cavity 704a for receiving the porous element (not shown) and an exit tube 705.

The cavity 704a that holds the porous plastic was 0.079 inches in depth and a 3-mm diameter punch of porous material placed it neatly into the cavity. The valve slide 706 was assembled with the porous plastic in place. In addition to the different porous plastic properties, a second variable is the exit tube 705 that was secured with a hex nut 707 on the valve. The length of the exit tube was 1.0 inches, and the outer diameter of the exit tube 705 remained 0.0625 inches, but the inner diameter was varied for purposes of the experiment. Once the valve slide 706 was assembled, it was placed into a CryOmega spray device, available from Cryo-Concepts, Bethlehem, Pa., along with a 16 g cylinder of liquid nitrous oxide or liquid carbon dioxide. Once the cylinder was pierced and gas was in the device, the flow channel was opened, and gas was allowed to flow for 5 seconds. The appearance of the gas as a spray, liquid, or solid was recorded in the results table (Tables 2-6: Nitrous Oxide and Table 7: Carbon Dioxide) along with the amount of gas dispensed (g). The material of the exit tube 705 is also listed.

TABLE 2

Nitrous Oxide

| PE (porous element) | Pore Size (microns) | Exit Tubing ID | Wt (g) Sprayed per 5 Seconds | Observation of Spray |
|---|---|---|---|---|
| PM-2 | 4-7 | 0.004 | 0.36 | Spray |
| PM-2 | 4-7 | 0.005 | 0.57 | Spray |
| PM-2 | 4-7 | 0.007 | 0.27 | Spray |
| PM-2 | 4-7 | 0.010 | 0.30 | Spray |
| PM-2 | 4-7 | 0.010 | 0.61 | Spray |
| PM-2 | 4-7 | 0.010 | 0.62 | Spray |
| PM-2 | 4-7 | 0.020 | 0.74 | Light Spray, Liquid around tube opening |
| PM-2 | 4-7 | 0.020 | 0.76 | Spray |
| PM-2 | 4-7 | 0.020 | 0.59 | Spray, Liquid around the tube opening |
| PM-2 | 4-7 | 0.030 | 0.44 | Liquid, some spray initially |
| PM-2 | 4-7 | 0.040 | 0.65 | Liquid with light force |
| PM-2 | 4-7 | 0.040 | 0.58 | Liquid with light force |

TABLE 3

Nitrous Oxide

| PE (porous element) | Pore Size (microns) | Exit Tubing ID | Wt (g) Sprayed per 5 Seconds | Observation of Spray |
|---|---|---|---|---|
| PM-3 | 7 to 14 | 0.004 | 0.61 | Spray |
| PM-3 | 7 to 14 | 0.005 | 0.80 | Spray |
| PM-3 | 7 to 14 | 0.007 | 1.25 | Spray |
| PM-3 | 7 to 14 | 0.010 | 1.10 | Spray |
| PM-3 | 7 to 14 | 0.010 | 0.66 | Spray |
| PM-3 | 7 to 14 | 0.010 | 1.23 | Spray |
| PM-3 | 7 to 14 | 0.020 | 0.93 | Spray |
| PM-3 | 7 to 14 | 0.020 | 0.85 | Spray |
| PM-3 | 7 to 14 | 0.020 | 0.91 | Spray |
| PM-3 | 7 to 14 | 0.030 |  | Spray with Liquid around Orifice |
| PM-3 | 7 to 14 | 0.040 | 0.22 | Liquid |
| PM-3 | 7 to 14 | 0.040 | 0.73 | Liquid with some light force |

TABLE 4

Nitrous Oxide

| PE (porous element) | Pore Size (microns) | Exit Tubing ID | Wt (g) Sprayed per 5 Seconds | Observation of Spray |
|---|---|---|---|---|
| PM-6 | 30 to 60 | 0.004 | 0.61 | Spray |
| PM-6 | 30 to 60 | 0.005 | 1.33 | Spray |
| PM-6 | 30 to 60 | 0.007 | 2.07 | Spray |
| PM-6 | 30 to 60 | 0.010 | 2.78 | Spray |
| PM-6 | 30 to 60 | 0.010 | 2.16 | Spray |
| PM-6 | 30 to 60 | 0.010 | 1.81 | Spray |
| PM-6 | 30 to 60 | 0.020 | 1.31 | Spray |
| PM-6 | 30 to 60 | 0.020 | 1.28 | Spray |
| PM-6 | 30 to 60 | 0.020 | 1.21 | Spray |
| PM-6 | 30 to 60 | 0.030 | 1.35 | Spray |
| PM-6 | 30 to 60 | 0.040 | 1.01 | Liquid |
| PM-6 | 30 to 60 | 0.040 | 0.98 | Liquid |

TABLE 5

Nitrous Oxide

| PE (porous element) | Pore Size (microns) | Exit Tubing ID | Wt (g) Sprayed per 5 Seconds | Observation of Spray |
|---|---|---|---|---|
| PM-8 | 3 to 5 | 0.004 | 0.64 | Spray |
| PM-8 | 3 to 5 | 0.005 | 0.94 | Spray |
| PM-8 | 3 to 5 | 0.007 | 1.01 | Spray |
| PM-8 | 3 to 5 | 0.010 | 0.86 | Spray |
| PM-8 | 3 to 5 | 0.010 | 0.78 | Spray |
| PM-8 | 3 to 5 | 0.010 | 0.77 | Spray |
| PM-8 | 3 to 5 | 0.020 | 0.83 | Spray |
| PM-8 | 3 to 5 | 0.020 | 0.69 | Spray |
| PM-8 | 3 to 5 | 0.020 | 0.67 | Spray |
| PM-8 | 3 to 5 | 0.030 | 0.67 | Liquid |
| PM-8 | 3 to 5 | 0.040 | 0.7 | Liquid |
| PM-8 | 3 to 5 | 0.040 | 0.62 | Liquid |

TABLE 6

Nitrous Oxide

| PE (porous element) | Pore Size (microns) | Exit Tubing ID | Wt (g) Sprayed per 5 Seconds | Observation of Spray |
|---|---|---|---|---|
| PM-7 | 1 to 3 | 0.004 | 0.02 | Barely any Spray |
| PM-7 | 1 to 3 | 0.005 | 0.03 | Barely any Spray |
| PM-7 | 1 to 3 | 0.007 | 0.03 | Barely any Spray |
| PM-7 | 1 to 3 | 0.010 | 0.02 | Barely any Spray |

TABLE 6-continued

Nitrous Oxide

| PE (porous element) | Pore Size (microns) | Exit Tubing ID | Wt (g) Sprayed per 5 Seconds | Observation of Spray |
|---|---|---|---|---|
| PM-7 | 1 to 3 | 0.010 | 0.03 | Barely any Spray |
| PM-7 | 1 to 3 | 0.010 | 0.02 | Barely any Spray |
| PM-7 | 1 to 3 | 0.020 | 0.02 | Barely any Spray |
| PM-7 | 1 to 3 | 0.020 | 0.04 | Barely any Spray |
| PM-7 | 1 to 3 | 0.020 | 0.03 | Barely any Spray |
| PM-7 | 1 to 3 | 0.030 | 0.02 | Barely any Spray |
| PM-7 | 1 to 3 | 0.040 | 0.02 | Barely any Spray |
| PM-7 | 1 to 3 | 0.040 | 0.02 | Barely any Spray |

TABLE 7

Carbon Dioxide

| PE (porous element) | Pore Size (microns) | Exit Tubing ID | Wt (g) Sprayed per 5 Seconds | Observation of Spray |
|---|---|---|---|---|
| PM-2 | 4-7 | 0.004 | 0.90 | Spray |
| PM-2 | 4-7 | 0.005 | 1.19 | Spray |
| PM-2 | 4-7 | 0.007 | 2.44 | Spray |
| PM-2 | 4-7 | 0.010 | 1.53 | Spray |
| PM-2 | 4-7 | 0.010 | 1.62 | Spray |
| PM-2 | 4-7 | 0.010 | 1.17 | Spray |
| PM-2 | 4-7 | 0.020 | 1.18 | Spray |
| PM-2 | 4-7 | 0.020 | 1.59 | Spray |
| PM-2 | 4-7 | 0.020 | 1.16 | Spray |
| PM-2 | 4-7 | 0.030 | 1.17 | Spray with some liquid |
| PM-2 | 4-7 | 0.040 | 0.87 | Light spray |
| PM-2 | 4-7 | 0.040 | 0.58 | Light Spray |

Table 8 below summarizes the key attributes of each porous element (PE) tested when nitrous oxide gas was expressed as a liquid with an ID of 0.040 in. In one case, PM-7, none of the combinations of (micro) porous elements plus Exit Tubing ID allowed any flow of gas. Thus, showing that the (micro) porous channels within the porous element must allow a sufficient amount of pressurized gas (fluid) to flow.

TABLE 8

Nitrous Oxide Results

| PE (porous element) Pore Size | Porosity % | Thickness(in) | Thickness(mm) | Flow Rate (Dispense Rate) |
|---|---|---|---|---|
| 1-3 | 25-30 | 0.079 | 2 | 0.02 |
| 3-5 | 30-40 | 0.04 | 1 | 0.62 |
| 4-7 | 40-45 | 0.059 | 1.5 | 0.98 |
| 7-14 | 45-55 | 0.059 | 1.5 | 0.73 |
| 30-60 | 50-60 | 0.059 | 1.5 | 0.58 |

For carbon dioxide the results were slightly different. Only a single (micro) porous element (ME), PM-2, was tested across all the exit tube 405 sizes. The results showed that the rheological state could be modified with the change in inner diameter of the exit tube 405, while the length remained constant at 1.0 inches. Using the exit tubing with the smallest lumen dispensed ice crystals of decreased size and slowed the flow rate (dispense rate).

EXAMPLE 2

Pentafluoroethane

A second flow modulation model system was constructed using a 12 oz. tank of pentafluoroethane, which is a common refrigerant. The pressure of pentafluoroethane is 175 psig. A 3 mm punch of each porous plastic was placed into the assembly and tested. The flow channel in this example experiment included a valve to turn on/off the liquefied gas flow into a cavity that held the 3 mm punch of porous plastic. The (micro) porous elements (ME) and exit tubing tested were the same as with carbon dioxide and nitrous oxide in Example 1. Once assembled, the gas (fluid) pressure was turned on, and the type of flow was recorded as a spray or liquid drops. The results are shown in Table 9. The data showed that across the spectrum of pore sizes tested, the dispensed fluid could be varied from fast spray to drops.

TABLE 9

Pentafluoroethane Results

| PE (porous element) | Gas | Pore Size (microns) | Observation of Spray |
|---|---|---|---|
| PM-7 | pentafluoroethane | 1-3 | Dripping Liquid |
| PM-8 | pentafluoroethane | 3-5 | Light Spray |
| PM-2 | pentafluoroethane | 4-7 | Light Spray |
| PM-3 | pentafluoroethane | 7-14 | Gentle Spray |
| PM-6 | pentafluoroethane | 30-60 | Heavy Spray |

EXAMPLE 3

WD-40® Multi-Use Product

The commercial product, WD-40® Multi-Use Product was used to demonstrate that flow control using the low-pressure flow system of the invention is also applicable to other devices that use high pressure gases to propel a liquid. WD-40® Multi-Use Product is commonly used to lubricate joints and hinges. Its commercial design has the downside of spraying the lubricant wildly and is difficult to control. For purposes of the experiment, the commercial valve was modified with a piece of porous material in accordance with the invention. The 1.0 inch exit tube was then inserted, and the valve opened. Upon actuation of the can, the WD-40® fluid dripped rather than sprayed in a cup. Thus, the flow modulation of the invention was effective with an aerosol controlling the gas (fluid) pressure while pushing a secondary material.

Pressurized fluids such as liquefied gases and aerosols (mixtures of a pressurized gas propellant and another fluid to be dispensed) are used in industrial settings, medical treatment and in households. Pressurized fluids are typically sealed in a metal container under pressure and dispensed by opening a valve, typically a push-button or trigger valve. The pressurized fluid is dispensed from the container through a single small hole through an aperture or nozzle or through a dispenser cap connected to the valve emerging as a gaseous mist, a spray, or a liquid stream. Due to the pressures within the containers and the limitations of design of the nozzle or dispenser caps, the dispensed fluids often have high flow rates (dispense rates) dictated by the pressure within the container and are difficult to control, especially when a user attempts to dispense only a small volume of fluid or precisely direct the dispensed fluid. This can create potential safety issues or, at a minimum, makes pressurized fluids difficult to use, apply, and/or control when dispensing. One example of a widely used lubricant spray that is notoriously difficult to control when dispensing is WD-40®. The experiments demonstrated the effect of the invention on the spray characteristics and control of WD-40®. Table 10 shows the porous materials used in the study.

TABLE 10

Porous Materials

| Pore Size (microns) | Median Pore Size (Microns) | Thickness (in.) |
|---|---|---|
| 4 to 7 | 5.5 | 0.058 |
| 5 to 10 | 7.5 | 0.12 |
| 7 to 14 | 10.5 | 0.08 |
| 7 to 14 | 10.5 | 0.057 |
| 12 to 25 | 18.5 | 0.058 |
| 15 to 40 | 27.5 | 0.08 |
| 10 to 45 | 27.5 | 0.054 |
| 15 to 50 | 32.5 | 0.066 |
| 30 to 60 | 45 | 0.06 |

For the experiment set-up, a high-pressure aluminum gas cylinder was filled with WD-40® using a funnel. A depressor operated valve was threaded onto the cylinder until hand tight. The adaptor body was inserted into one end of the connector. The other end of the connector was connected to the compressor. The compressor was turned on to approximately 100 psi. The adaptor body was connected to the cylinder and the trigger of the connector was held down to regulate the pressure. The trigger was released when the pressure read 100 psi. A 3 mm punch of the first porous material sample was inserted into the first valve adaptor/tubing assembly. The valve adaptor/tubing assembly was affixed to the cylinder by pressing it down with Channellock pliers until it clicks and is properly seated. The handle and trigger are attached to the top of the valve adapter so that it snaps into place.

For the experiment, the timer was started, and the cylinder was flipped upside down. The cylinder was held over a cardboard box to collect any mess. The trigger was held down for 5 seconds to release the WD-40®. Observations were taken of the phase and properties of the lubricant. The handle, trigger, and valve adaptor were removed from the cylinder. Then a 3 mm punch of the next sample of porous material was inserted into the back of the valve adaptor. The experiment was repeated for each sample of porous material. The cylinder was reconnected to the compressor every 2 to 3 runs in order to maintain a constant pressure in the cylinder. The experiment was then repeated with each sample of tubing.

Tables 11 through 22 show the results of the experiment for each pore size.

TABLE 11

Results using porous material 4-7 microns

| Pore Size (Microns) | Pore Thickness (in.) | Exit Tubing ID (in.) | Observation of Spray |
|---|---|---|---|
| 4 to 7 | 0.058 | 0.004 | Few Droplets |
| 4 to 7 | 0.058 | 0.005 | Droplets |
| 4 to 7 | 0.058 | 0.01 | Droplets |
| 4 to 7 | 0.058 | 0.02 | Thin Stream |
| 4 to 7 | 0.058 | 0.03 | Thin Stream |
| 4 to 7 | 0.058 | 0.04 | Stream |
| 4 to 7 | 0.058 | 0.04 | Stream |

TABLE 12

Results using porous material 5 to 10 microns

| Pore Size (Microns) | Pore Thickness (in.) | Exit Tubing ID (in.) | Observation of Spray |
|---|---|---|---|
| 5 to 10 | 0.12 | 0.004 | Few Droplets |
| 5 to 10 | 0.12 | 0.005 | Thin Stream and Droplets |
| 5 to 10 | 0.12 | 0.01 | Thin Stream and Droplets |
| 5 to 10 | 0.12 | 0.02 | Stream |
| 5 to 10 | 0.12 | 0.03 | Stream |
| 5 to 10 | 0.12 | 0.04 | Stream |
| 5 to 10 | 0.12 | 0.04 | Stream |

TABLE 13

Results using porous material 7 to 14 microns

| Pore Size (Microns) | Pore Thickness (in.) | Exit Tubing ID (in.) | Observation of Spray |
|---|---|---|---|
| 7 to 14 | 0.08 | 0.004 | Few Droplets |
| 7 to 14 | 0.08 | 0.005 | Droplets |
| 7 to 14 | 0.08 | 0.01 | Droplets |
| 7 to 14 | 0.08 | 0.02 | Droplets |
| 7 to 14 | 0.08 | 0.03 | Droplets |
| 7 to 14 | 0.08 | 0.04 | Many Droplets |
| 7 to 14 | 0.08 | 0.04 | Thin Stream and Droplets |

TABLE 14

Results using porous material 7 to 14 microns/0.057 thickness

| Pore Size (Microns) | Pore Thickness (in.) | Exit Tubing ID (in.) | Observation of Spray |
|---|---|---|---|
| 7 to 14 | 0.057 | 0.004 | Few Droplets |
| 7 to 14 | 0.057 | 0.005 | Droplets |
| 7 to 14 | 0.057 | 0.01 | Droplets |
| 7 to 14 | 0.057 | 0.02 | Droplets |
| 7 to 14 | 0.057 | 0.03 | Thin Stream and Droplets |
| 7 to 14 | 0.057 | 0.04 | Thin Stream and Droplets |
| 7 to 14 | 0.057 | 0.04 | Thin Stream and Droplets |

TABLE 15

Results using porous material 12 to 25 microns

| Pore Size (Microns) | Pore Thickness (in.) | Exit Tubing ID (in.) | Observation of Spray |
|---|---|---|---|
| 12 to 25 | 0.058 | 0.004 | Few Droplets |
| 12 to 25 | 0.058 | 0.005 | Few Droplets |
| 12 to 25 | 0.058 | 0.01 | Thin Stream |
| 12 to 25 | 0.058 | 0.02 | Stream |
| 12 to 25 | 0.058 | 0.03 | Stream |
| 12 to 25 | 0.058 | 0.04 | Stream |
| 12 to 25 | 0.058 | 0.04 | Stream |

TABLE 16

Results using porous material 15 to 40 microns

| Pore Size (Microns) | Pore Thickness (in.) | Exit Tubing ID (in.) | Observation of Spray |
|---|---|---|---|
| 15 to 40 | 0.08 | 0.004 | Few Droplets |
| 15 to 40 | 0.08 | 0.005 | Few Droplets |
| 15 to 40 | 0.08 | 0.01 | Many Droplets |
| 15 to 40 | 0.08 | 0.02 | Many Droplets |
| 15 to 40 | 0.08 | 0.03 | Thin Stream and Droplets |
| 15 to 40 | 0.08 | 0.04 | Stream |
| 15 to 40 | 0.08 | 0.04 | Stream |

TABLE 17

Results using porous material 10 to 45 microns/0.054 thickness

| Pore Size (Microns) | Pore Thickness (in.) | Exit Tubing ID (in.) | Observation of Spray |
|---|---|---|---|
| 10 to 45 | 0.054 | 0.004 | Few Droplets |
| 10 to 45 | 0.054 | 0.005 | Droplets |
| 10 to 45 | 0.054 | 0.01 | Stream |
| 10 to 45 | 0.054 | 0.02 | Stream |
| 10 to 45 | 0.054 | 0.03 | Stream |
| 10 to 45 | 0.054 | 0.04 | Stream |
| 10 to 45 | 0.054 | 0.04 | Stream |

TABLE 18

Results using porous material 15 to 50 microns

| Pore Size (Microns) | Pore Thickness (in.) | Exit Tubing ID (in.) | Observation of Spray |
|---|---|---|---|
| 15 to 50 | 0.066 | 0.004 | Few Droplets |
| 15 to 50 | 0.066 | 0.005 | Few Droplets |
| 15 to 50 | 0.066 | 0.01 | Stream |
| 15 to 50 | 0.066 | 0.02 | Stream |
| 15 to 50 | 0.066 | 0.03 | Stream |
| 15 to 50 | 0.066 | 0.04 | Stream |
| 15 to 50 | 0.066 | 0.04 | Stream |

TABLE 19

Results using porous material 30 to 60 microns

| Pore Size (Microns) | Pore Thickness (in.) | Exit Tubing ID (in.) | Observation of Spray |
|---|---|---|---|
| 30 to 60 | 0.06 | 0.004 | Few Droplets |
| 30 to 60 | 0.06 | 0.005 | Few Droplets |
| 30 to 60 | 0.06 | 0.01 | Droplets |
| 30 to 60 | 0.06 | 0.02 | Droplets |
| 30 to 60 | 0.06 | 0.03 | Stream |
| 30 to 60 | 0.06 | 0.04 | Stream |
| 30 to 60 | 0.06 | 0.04 | Stream |

Tables 20 through 22 show the results of regression analysis on the data collected during the experiment.

TABLE 20

Regression
Regression Statistics

| | |
|---|---|
| Multiple R | 0.760220463 |
| R Square | 0.577935152 |
| Adjusted R Square | 0.556474228 |
| Standard Error | 1.385441055 |
| Observations | 63 |

TABLE 21

Regression

| | df | SS | MS | F | Significance F |
|---|---|---|---|---|---|
| Regression | 3 | 155.0700922 | 51.69003 | 26.92965 | 4.24191E−11 |
| Residual | 59 | 113.2473681 | 1.919447 | | |
| Total | 62 | 268.3174603 | | | |

TABLE 22

Regression

| | Coefficients | Standard Error | t Stat | P-value | Lower 95% | Upper 95% | Lower 95.0% | Upper 95.0% |
|---|---|---|---|---|---|---|---|---|
| Intercept | 0.582371201 | 0.866652713 | 0.671978 | 0.504221 | −1.151796872 | 2.316539274 | −1.151796872 | 2.316539274 |
| Median Pore Size | 0.015586366 | 0.014634752 | 1.065024 | 0.291204 | −0.013697705 | 0.044870436 | −0.013697705 | 0.044870436 |
| Porous Element Thickness | 8.63658254 | 9.350521342 | 0.923647 | 0.359432 | −10.07376745 | 27.34693253 | −10.07376745 | 27.34693253 |
| Tubing ID | 107.2763411 | 12.04737859 | 8.904538 | 1.65E−12 | 83.16959221 | 131.38309 | 83.16959221 | 131.38309 |

Regression analysis showed that 58% of the output variation could be explained by the variables pore size, porous element thickness, and tubing ID. This shows that there are also other parameters of the liquid or material selections that also influence liquid flow characteristics.

A user can adjust the desired rheological output characteristics of the liquid stream under pressure from small droplets to a controlled stream by adjusting one or more of the variables.

The coefficients can change as the user changes porous materials, diameters of the tubing and the operating pressure of the system to be controlled.

The invention provides a flow modulation device for controlling a rheological state of a dispensed pressurized fluid. The flow modulation devices of the invention include a porous element and an exit tube. The porous element is in fluid communication with a distal end of an outlet tube and receives pressurized fluid in a first rheological state. The porous element includes channels that divide a flow channel into flow paths through which the pressurized fluid flows. The porous element modulates the flow of the pressurized fluid allowing a user to control the state and flow rate (dispense rate) of the dispensed fluid.

The claimed invention is:

1. A method of controlling an output rheological state of a dispensed pressurized fluid as the fluid leaves an exit tube, the rheological state including a combination of flow rate and material phases of the pressurized fluid, and the method comprising:

selecting the pressurized fluid and a desired output rheological state of the pressurized fluid as the pressurized fluid leaves the exit tube, wherein the pressurized fluid input rheological state is different than the output rheological state of the pressurized fluid as the fluid leaves the exit tube;

determining a fluid pressure of the input rheological state of the pressurized fluid;

selecting a porous element based upon the desired output rheological state of the fluid, the porous element in fluid communication with the pressurized fluid in its input rheological state and including:

a) a material type;

b) a pore size;

c) a porosity;

d) a diameter; and e) a length dividing, with the porous element, the pressurized fluid into a plurality of flow paths when the pressurized fluid flows through the porous element;

controlling the flow of the pressurized fluid with the plurality of flow paths to produce a desired mass flow rate of the pressurized fluid;

selecting the exit tube based upon the desired output rheological state of the fluid, the exit tube in fluid communication with the pressurized fluid from the porous element and including:

f) a material type;

g) an inner diameter;

h) an outer diameter; and i) a length; and refocusing, with the exit tube, the pressurized fluid from the plurality of flow paths;

selecting at least one of an alternative porous element and an alternative exit tube having at least one different parameter selected from the group of parameters a) through i) above to achieve and maintain the desired output rheological state of the pressurized fluid leaving the exit tube when the output rheological state does not match the desired output rheological state; and dispensing the pressurized fluid in the desired output rheological state based on the interaction of the elements a) through i) above.

2. A method of claim 1, wherein the output rheological state includes at least one of the following: a spray or droplets or a stream.

3. A method claim 1, wherein the output rheological state includes a spray including droplets in a gas.

4. A method of claim 3, wherein the spray is an aerosol.

5. A method of claim 3, wherein the spray is a vapor.

6. A method of claim 1, wherein the output rheological state includes a spray including solid particles in a gas.

7. A method of claim 1, wherein the output rheological state includes droplets.

8. A method of claim 1, wherein the output rheological state includes a stream.

9. A method of claim 1, wherein the pressurized fluid is a cryogen, a refrigerant, or a propelled material.

10. A method of claim 1, wherein the pressurized fluid includes at least one of a pressurized fluid from the following classes of gases: fluorocarbons, chlorofluorocarbons, hydrochlorofluorocarbons, hydrofluorocarbons, and hydrofluoroolefins, organic propellants, hydrocarbons.

11. A method of claim 1, wherein the pressurized fluid includes at least one of the following gases: pentafluoroethane, difluoromethane, trifluoromethane, dichlorodifluoromethane, dichlorofluoromethane, chlorodifluoromethane, tetrafluoroethane, 1,1,1,-trifluoroethane, 2,3,3,3-tetrafluoropropene, cis-1,1,1,4,4,4-hexafluoro-2-butene, trans-1,1,1,4,4,4-hexafluoro-2-butene, tetrafluoromethane, monochlorotrifluoromethane, hexafluoroethane, monobromotri fluoromethane, monochlorodifluoromethane, monochloropenta fluoroethane,,1,2-dichloro-, 1,1,2,2-tetrafluoroethane, trichloromonofluoromethane, 1,1,2-trichloro-, 1,2,2-trifluoroethane and 1,1-difluoro ethane, and isobutane.

12. A method of claim 1, wherein the pressurized fluid includes at least one of the following pressurized fluids: nitrous oxide, carbon dioxide, dimethyl ether, propane, and butane.

13. A method of claim 1, wherein the pressurized fluid is a propelled material that includes at least one of the following propelled materials: a food product, a medicine, a perfume, a cosmetic, a lubricant, a cleaning product, an insecticide, a fuel, and an additional fluid in contact with the propelled material.

14. The method of claim 1, wherein the porous element includes at least one of the following porous elements: a porous plastic, a porous glass, a sintered metal, and a packaged porous particle in a shape of the flow channel.

15. A method of claim 1 further comprising:

adjusting at least one parameter selected from the group of parameters b) through a) through e) characterizing the porous member to reduce the pressure and/or flow rate of the pressurized fluid leaving the exit tube.

16. A method of claim 1 further comprising:

adjusting at least one parameter selected from the group of parameters a) through e) characterizing the porous member to increase the pressure and/or flow rate of the pressurized fluid leaving the exit tube.

17. A method of claim 1 further comprising:

adjusting at least one parameter from the group of parameters f) through i) characterizing the exit tube to reduce the pressure and/or flow rate of the pressurized fluid leaving the exit tube.

18. A method of claim 1 further comprising:
adjusting at least one parameter from the group of parameters f) through i) characterizing the exit tube to increase the pressure and/or flow rate of the pressurized fluid leaving the exit tube.

\* \* \* \* \*